United States Patent
Weiss et al.

(10) Patent No.: US 7,273,945 B2
(45) Date of Patent: Sep. 25, 2007

(54) PREPARATION OF PHOSPHORUS-CONTAINING ALKOXYLATION PRODUCTS

(75) Inventors: Thomas Weiss, Mannheim (DE); Wolfgang Grape, Köln (DE); Rainer Elbert, Bergisch Gladbach (DE); Jan-Gerd Hansel, Köln (DE); Johannes Kaulen, Odenthal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 56 days.

(21) Appl. No.: 11/376,356

(22) Filed: Mar. 15, 2006

(65) Prior Publication Data
US 2006/0211878 A1    Sep. 21, 2006

(30) Foreign Application Priority Data
Mar. 18, 2005    (DE)    ............ 10 2005 012 596

(51) Int. Cl.
*C07R 9/02*    (2006.01)
(52) U.S. Cl. ............................................. 558/91
(58) Field of Classification Search .......... 558/91
See application file for complete search history.

(56) References Cited

U.S. PATENT DOCUMENTS

| 3,557,260 | A | | 1/1971 | Gurgiolo |
| 3,899,550 | A | * | 8/1975 | Demarcq ............ 558/91 |
| 4,086,194 | A | * | 4/1978 | Altscher et al. ........... 521/168 |

FOREIGN PATENT DOCUMENTS

| CN | 1034206 | 7/1989 |
| SU | 125035 | 3/1977 |

OTHER PUBLICATIONS

Yang, Jin-Fei; *Catalytical synthesis of tri(β-chloroethyl)phosphate over TiSiW1202 catalyst*; College of Chemistry and Environmental Sience, Nanjing Normal University, Peop. Rep. China. Yingyong Huaxue (2003), 20(2), 201-202.

* cited by examiner

*Primary Examiner*—Peter O'Sullivan
(74) *Attorney, Agent, or Firm*—Michael A. Miller

(57) ABSTRACT

The invention describes a process for preparing alkoxylated, phosphorus-containing compounds, using heterogeneous catalysts based on metal oxides of aluminum, so that the product can be worked up anhydrously.

6 Claims, No Drawings

PREPARATION OF PHOSPHORUS-CONTAINING ALKOXYLATION PRODUCTS

The invention relates to a process for preparing phosphorus-containing alkoxylation products by means of heterogeneous catalysts, the products being suitable for use as flame retardants in polyurethanes.

The preparation of phosphorus-containing alkoxylation products, particularly of organic phosphonates and halogen-substituted alkyl phosphates, is known to the skilled worker. Primarily phosphoric acid, phosphorous acid or phosphorus trihalide, preferably phosphorus trichloride, or phosphorus oxyhalide, especially phosphorus oxychloride, are used and are reacted with epoxides such as ethylene oxide, propylene oxide and/or epichlorohydrin. To increase the reaction rate it is common to use catalysts. For catalysts which operate homogeneously there are numerous versions known to the skilled worker.

Generally speaking, however, the alkoxylated products obtained have to be purified in systems which operate with homogeneous catalysis, which is costly and inconvenient. Aftertreatment is usually accomplished by an aqueous workup of the crude reaction products, in the course of which the catalyst is destroyed irreversibly and separated off.

BACKGROUND ART

This is described for example in DD 125 035, where deactivation and/or destruction of the titanium halide catalyst is achieved by adding a stoichiometric amount of water or by washing the phosphorus-containing alkoxylation products with water or alkalis.

Aftertreatments of this kind for destroying and/or deactivating the catalyst, however, have disadvantages. They necessitate reactors additionally; there is a deterioration in the space-time yield; and losses of product occur. The washing waters produced must be disposed of, which is costly and inconvenient. And, not least, the catalyst employed is lost to further use. Apart from the processes with homogeneous catalysis, the use of heterogeneous catalysts is largely unknown.

One heterogeneous catalysis system was recently described by Yang, Jin-Fei in *Yingyong Huaxue* 2003, 20 (2), 201-202, using TiSiW$_{12}$O$_{40}$/TiO$_2$, for the preparation of (ClCH$_2$CH$_2$O)$_3$PO. A disadvantage associated with the use of the catalyst is the comparatively costly and inconvenient preparation.

A continuous production method of 2-haloalkylated phosphates by means of heterogeneous catalysts is described in CN 1 034 206. In that case BeO is employed. The process permits the preparation of low-acid products (acid number<0.2 mg KOH/g solid) such as (MeCHClCH$_2$O)$_3$PO, (ClCH$_2$CHClCH$_2$O)$_3$PO, and (ClCH$_2$CH$_2$O)$_3$PO. A disadvantage associated with the use of the catalyst is the potential release of highly toxic beryllium salts.

U.S. Pat. No. 3,557,260 proposes the use of sulfates of various elements. The required reaction time is approximately 80 hours and is much longer, for economic operations, than the state of the art.

The object of the present invention was therefore to develop a process for preparing phosphorus-containing alkoxylation products, using heterogeneous catalysts, while avoiding the disadvantages of the prior art.

SUMMARY OF THE INVENTION

The solution to this problem, and hence the subject of the present invention, is a process for preparing low-acid, phosphorus-containing alkoxylation products by reacting phosphorus trihalides and/or phosphorus oxyhalides with alkylene oxides, with omission of additional water washing or alkali washing of the phosphorus-containing alkoxylation products, which comprises using alumina-containing, heterogeneous catalysts.

Surprisingly the phosphorus-containing alkoxylation products prepared by means of alumina-containing heterogeneous catalysts exhibit a much lower acid number than in the prior art. The other advantages of the process of the invention, based on heterogeneous, alumina-containing catalysts, lie in the easy, anhydrous separability of the catalyst from the starting substances and the reaction products. This ease of separation therefore makes it possible to do without costly and inconvenient product washing, and allows the production operation to be made more economic in relation to the prior art. The formation of acidic by-products is suppressed, as is apparent from the extremely low acid numbers of the phosphorus-containing alkoxylation products. Furthermore, in the case of a batchwise procedure, the catalyst employed can be used again.

DETAILED DESCRIPTION OF THE INVENTION

Phosphorus-containing reactants used in the process of the invention are preferably phosphorus trihalides and/or phosphorus oxyhalides, especially phosphorus trichloride and/or phosphorus oxychloride, and they are reacted, individually or in a mixture with one another, with the alkylene oxides. Examples of alkylene oxides are ethylene oxide, propylene oxide, styrene oxide, cyclohexene oxide, cyclopentene oxide, glycidyl ethers, epichlorohydrin, epoxidized polybutadiene, and epoxidized unsaturated oils. The alkylene oxides may also be used in a mixture with one another with the phosphorus trihalides and/or phosphorus oxyhalides. In this way it is possible to obtain phosphorus-containing alkoxylation products such as, for example, tri(chloropropyl) phosphate (TCPP), tri(chloroethyl) phosphate (TCEP), tri(chloropropyl) phosphite or tri(chloroethyl) phosphite.

In one particularly preferred embodiment propylene oxide and/or ethylene oxide are used as alkylene oxide.

As alumina-containing heterogeneous catalysts it is preferred to use compounds of the general formula (I)

$$[Al]_l 3+(B)_n b+]O_m \qquad (I)$$

in which

B is a metal or nonmetal from the group Li, Na, K, Mg, Ca, Sr, Ba, Sc, Y, Ln, Ti, Zr, Hf, V, Nb, Ta, Cr, Mo, W, B, Ga, In, Si, Ge, Sn, Pb, P, As, Sb, and Bi, b is the valence of the metal or nonmetal B and is an integer between 1 and 6, l, n, and m are numerical variables selectable independently from the numbers 0.0001 to 4.0000, so that:

$2 \cdot m = l \cdot 3 + n \cdot b$.

Examples of (mixed) metal oxides can be oxides of the elements of the transition group of the Periodic Table of the Elements, or oxides of the metals from groups 13-15 of the Periodic Table of the Elements. In this context, the term "Periodic Table of the Elements" is understood below to be that according to IUPAC (Nomenclature of Inorganic Chemistry 1989). Particular preference is given to the (mixed) metal oxides of groups 3-6, 13, and 14 of the Periodic Table of the Elements.

With particular preference B stands for ions of the element group

Na, K, Mg, Ca, Sc, Y, Ti, Zr, W, Si, and Sn, the other variables being as defined above.

With very particular preference in accordance with the invention $Al_2O_3$ is used in the process of the invention.

In accordance with the invention it is, however, also possible to use what are called alumina-containing mixed oxides as heterogeneous catalysts.

Examples of mixed oxides are the following:
$SiO_2*Al_2O_3$, $SnO_2*Al_2O_3$, $TiO_2*Al_2O_3$, $ZrO_2*Al_2O_3$, $WO_3*Al_2O_3$, $Sc_2O_3*Al_2O_3*Y_2O_3Al_2O_3$, $Na_2O*Al_2O_3$, $K_2O*Al_2O_3$, $MgO*Al_2O_3$, and $CaO*Al_2O_3$.

The mixed oxides here are to be interpreted not only as stoichiometric combinations but also as combinations of nonstoichiometric compositions. This is intended to be expressed by the symbol "*". In particular, combinations of metal oxides of one and the same element in different oxidation states are among those which may find use.

The heterogeneous catalysts employed are then composed, accordingly, of mixed metal oxides or metal nonmetal oxides, and may additionally have been modified by means of further chemical operations. Examples of such modifications include sulfating, hydrating or calcining.

For application as heterogeneous catalysts in the preparation of alkoxylated, phosphorus-containing compounds it is possible on the one hand for them to be physically prepared mixtures of alumina-containing metal oxides, such as by trituration or grinding, for example. Also possible, on the other hand, is the use of heterogeneous, alumina-containing catalysts obtained by means of sol/gel processes.

The heterogeneous alumina-containing catalysts are notable preferably for extensive insolubility in the reaction medium, and they can be removed from the reaction medium by simple, nonaqueous methods—for example, by simple filtration methods, or by utilizing centrifugal forces.

The process of the invention for preparing phosphorus-containing alkoxylation products by means of alumina-containing heterogeneous catalysts can be carried out either continuously or batchwise. Where the process is carried out batchwise it comprises adding the heterogeneous alumina-containing catalyst prior to the reaction of phosphorus trihalide and/or phosphorus oxyhalide with alkylene oxides, in two or more portions before or during the reaction. The reaction takes place at temperatures of 0 to 100° C. The reaction temperatures are situated preferably between 50 and 80° C. The reaction takes place at atmospheric pressure or under a slight overpressure of up to 1 MPa. The phosphorus trihalide and/or phosphorus oxyhalide is charged to the reaction vessel and, following the addition of catalyst, the alkylene oxide is metered in continuously. The reaction medium can be diluted by adding phosphorus-containing alkoxylation products with one of the reactants or separately therefrom. After the end of the metering of alkylene oxide an after-reaction phase is added on, at temperatures of 60 to 130° C., and, finally, volatile impurities are removed by vacuum distillation and/or nitrogen stripping at temperatures of 90 to 150° C. and pressures of up to <0.05 MPa. Volatile constituents are removed preferably at 130° C. and 40 mbar. No aftertreatment of the catalyst is necessary. In batch preparation processes of alkoxylated, phosphorus-containing compounds the alumina-containing catalysts are employed in an amount of 0.02% to 10% by weight, based on the phosphorus compound employed, and are added to the phosphorus-containing reactant.

Alternatively, in a continuous operation, the synthesis of alkoxylated, phosphorus-containing compounds can be operated using heterogeneous alumina-containing catalysts, in which case fluid bed reactors or tube reactors, for example, are employed. In this case the heterogeneous alumina-containing catalyst is the stationary phase and the reaction medium is the mobile phase. The reaction conditions are similar to those already described above in relation to the batchwise procedure.

EXAMPLES

Example 1

6 g of $Al_2O_3$ are weighed out together with $POCl_3$ (76.8 g, 0.5 mol) into a flask and left to stand under reduced pressure overnight. The amount of $POCl_3$ is then ascertained and supplemented. Subsequently trichloropropyl phosphate (TCPP) (100 g, 0.3 mol) is added and propylene oxide (102 g, 1.75 mol) is metered in over the course of 4 h. This is followed by stirring at 45° C. for 2 h.

Yield of TCPP prepared: 158 g, 96% of theory, based on $POCl_3$.

Example 2

| Catalyst | $T_R$ [° C.] | $^{31}P$ NMR [mol % TCPP] 0 to −5.5 ppm | Residual PO [GC area %] | OP(Oiso)3 | OP(On)3 | OP(Oiso)2(On) | OP(Oiso)(On)2 | TCPP ether | 2-MP | SZ mg KOH/g sample | AAS [ppm metal] |
|---|---|---|---|---|---|---|---|---|---|---|---|
| $TiCl_4$ not inventive | 65 | | 0.01 | 66.3 | 0.2 | 25.6 | 3.7 | 2.9 | 0.1 | | |
| $SiO_2Al_2O_3$ | 75 | 97.1 | 2.92 | 48.2 | 0.8 | 31.7 | 8.4 | 3.1 | 0.0 | 8.9 | <1 |
| $Al_2O_3$ | 75 | 98.2 | 4.84 | 50.0 | 0.5 | 29.7 | 6.3 | 3.3 | 0.0 | <1.0 | 18 |
| $Al_2O_3/MgO$ | 75 | 96.3 | 6.21 | 51.7 | 0.5 | 23.9 | 5.2 | 2.5 | 0.0 | <1.0 | |

General operating instructions: 5 g of $POCl_3$ are introduced and the catalyst (1 g) is added. The mixture is then heated to 50° C. and by means of a Telab pump model BF 411/30 (pump setting HUB [stroke]=30, delivery=50%= about 0.5 ml/min) a mixture of 11.7 g (7 ml) of $POCl_3$ and 20.9 g (25.1 ml) of propylene oxide is added dropwise. The temperature is maintained between 40 and 50° C. (60 and 70° C.) by means of a water bath. After the end of the addition (GC/NMR) there is a subsequent stirring time of 180 minutes at 50° C. (70° C.) with subsequent analysis by means of GC and 31P-NMR, determination of acid number, and determination of metal content by means of atomic absorption spectroscopy.

What is claimed is:

1. A process for preparing phosphorus-containing alkoxylation products by reacting phosphorus trihalides and/or phosphorus oxyhalides with alkylene oxides, with omission of additional water washing or alkali washing of the phosphorus-containing alkoxylation products, which comprises using alumina-containing heterogeneous catalysts.

2. A process as claimed in claim 1, wherein catalysts used are compounds of the formula (I)

$$[Al)_l 3+(B)_n b+]O_m \qquad (I)$$

in which
B is a metal or nonmetal from the group Li, Na, K, Mg, Ca, Sr, Ba, Sc, Y, Ln, Ti, Zr, Hf, V, Nb, Ta, Cr, Mo, W, B, Ga, In, Si, Ge, Sn, Pb, P, As, Sb, and Bi, b is the valence of the metal or nonmetal B and is an integer between 1 and 6, l, n, and m are numerical variables selectable independently from the numbers 0.0001 to 4.0000, so that:

$$2 \cdot m = 1 \cdot 3 + n \cdot b.$$

3. A process as claimed in claim 1, wherein alumina-containing catalysts used are mixed oxides from the group $SiO_2 * Al_2O_3$, $SnO_2 * Al_2O_3$, $TiO_2 * Al_2O_3$, $ZrO_2 * Al_2O_3$, $WO_3 * Al_2O_3$, $Sc_2O_3 * Al_2O_3$, $Y_2O_3 * Al_2O_3$, $Na_2O * Al_2O_3$, $K_2O * Al_2O_3$, $MgO * Al_2O_3$, and $CaO * Al_2O_3$.

4. A process as claimed in claim 1, which is carried out continuously or batchwise.

5. A process as claimed in claim 1 or 2, wherein Al2O3 or SiO2*Al2O3 is used as alumina-containing catalyst.

6. A process as claimed in claim 1, wherein propylene oxide and/or ethylene oxide are used as alkylene oxide.

* * * * *